(12) United States Patent
Huber et al.

(10) Patent No.: US 7,185,650 B2
(45) Date of Patent: Mar. 6, 2007

(54) SYSTEMS AND METHODS FOR DETERMINING A MINIMUM EFFECTIVE DOSE OF AN INHALED DRUG FOR AN INDIVIDUAL PATIENT AT A GIVEN TIME

(76) Inventors: Arie Huber, 14 Hatichon St., Haifa (IL) 32297; Yakov Reznikov, 99 Derech Hayam St., Haifa (IL) 34746; Paltiel Weiner, 61 Hadar St. P.O. Box 5431, Caesarea (IL); Eli Toister, Ma'Ale Shomron D.N., Lev Hashomron (IL) 44852

( * ) Notice: Subject to any disclaimer, the term of this patent is extended or adjusted under 35 U.S.C. 154(b) by 746 days.

(21) Appl. No.: 10/322,443

(22) Filed: Dec. 19, 2002

(65) Prior Publication Data

US 2004/0118398 A1    Jun. 24, 2004

(51) Int. Cl.
*A61M 16/00* (2006.01)
(52) U.S. Cl. .............................. 128/204.23; 128/203.13
(58) Field of Classification Search ........... 128/200.14, 128/200.22, 200.23, 203.12, 203.14, 203.15, 128/204.23, 204.26, 920; 600/533, 538
See application file for complete search history.

(56) References Cited

U.S. PATENT DOCUMENTS

| | | | | |
|---|---|---|---|---|
| 3,991,304 | A * | 11/1976 | Hillsman ..................... | 600/538 |
| 5,167,506 | A * | 12/1992 | Kilis et al. ................... | 434/262 |
| 5,724,986 | A | 3/1998 | Jones, Jr. et al. | |
| 5,826,570 | A | 10/1998 | Goodman et al. | |
| 6,123,068 | A * | 9/2000 | Lloyd et al. ............ | 128/200.24 |
| 6,348,209 | B2 * | 2/2002 | Placke et al. ............... | 424/435 |
| 6,467,477 | B1 * | 10/2002 | Frank et al. ........... | 128/203.23 |
| 6,733,464 | B2 * | 5/2004 | Olbrich et al. ............... | 600/538 |

OTHER PUBLICATIONS

Weiner et al. Characteristics of asthma in the elderly. Eur Respir J 1998;12 (3):564-8.
Kamada et al. Issues in the use of inhaled glucocorticoids. Am J Respir Crit Care Med 1996;153:1739-48.
Littlewood JM, Johnson AW, Edwards PA, et al. Growth retardation in asthmatic children treated with inhaled beclomethasone dipropionate. Lancet 1988;i:115-6, Wales JKH, Barnes ND, Swift PGF.
Growth retardation in children on steroids in asthma. Lancet 1991;338:1535-6, Wolthers OD, Pederson S.
Controlled study of linear growth in asthmatic children during treatment with inhaled corticosteroids. Pediatrics 1992;89:839-42., Wolthers OD, Pederson S.
Short-term growth during treatment with inhaled fluticasone propionate and beclomethasone dipropionate. Arch Dis Child 1993;68:673-6, Prifitsk K, Milner AD, Conway E, et al.
Dahl R, Lundback B, Malo J-L. A dose ranging study of fluticasone propionate in adult patients with moderate asthma. Chest 1993;104:1352-8.
Nikolaizik et al. Nocturnal cortisol secretion in healthy adults before and after inhalation of budesonide. Am J Respir Crit Care Med 1996;153:97-101.

(Continued)

*Primary Examiner*—Teena Mitchell
*Assistant Examiner*—Annette F. Dixon
(74) *Attorney, Agent, or Firm*—Mark M. Friedman (57) ABSTRACT

A system and method for determining a minimum effective dose of an inhaled drug for an individual patient at a given time. The system includes an apparatus to measure a performance measurement of the patient and a data processor capable of communication with the apparatus. The data processor provides a computed minimum effective dose for the individual patient by applying a predetermined rule the performance measurement. The method includes measuring a performance measurement of the patient, communicating the performance measurement to a data processor and computing a minimum effective dose for the patient by applying a predetermined rule to the performance measurement within the data processor.

12 Claims, 5 Drawing Sheets

OTHER PUBLICATIONS

Adrenal function in asthma. Arch Dis Child 1990;65:838-40.

Donnelly et al. Effects of budesonide and fluticasone on 24-hour plasma cortisol. Am J Respir Crit Care Med 1997;156:1746-51.

I J M Doull; (downloaded from www.archdischild.com on Sep. 5, 2006); The Effect of Asthma and its Treatment on Growth.

Paltiel Weiner et al. CHEST—The Cardiopulmonary and Critical Care Journal—"Nocturnal Cortisol Secretion in Asthmatic Patients After Inhalation of Flucticasone Propionate".

* cited by examiner

SYSTEMS AND METHODS FOR DETERMINING A MINIMUM EFFECTIVE DOSE OF AN INHALED DRUG FOR AN INDIVIDUAL PATIENT AT A GIVEN TIME

FIELD AND BACKGROUND OF THE INVENTION

The present invention relates to systems and methods for determining a minimum effective dose of an inhaled drug for an individual patient at a given time and, more particularly, to systems and methods for computing, and optionally delivering a minimum effective dose of an inhaled medication based upon results of a single measurement of a pulmonary performance indicator immediately prior to inhalation of the medication. The invention is expected to find special utility in care and treatment of chronic asthma patients.

Metered dose inhalers are widely employed to treat respiratory conditions. Typically, a metered dose inhaler delivers a predetermined dose of an aerosolized drug with each actuation of a delivery mechanism. The most common configuration employs pressurized gas to move a drug through a narrow opening where the drug is aerosolized. The device is typically positioned in the mouth or nostril(s) of a patient so that the aerosolized drug is delivered to the appropriate region of the airway Metered dose inhalers share a common inherent disadvantage. Although delivery is exact, dosage is formulated based upon research on large populations of patients. This inherent disadvantage creates two problems. The first problem is that patients may take more medication than they actually require. The second problem is that some patients may require more medication than recommended on some occasions.

The number of patients using metered dose inhalers on a routine basis is quite large. For example, asthma affects approximately 10–15% of children and 5–10% of adults. The American Thoracic Society, the American Lung Association and the European Respiratory Society (Kamada et al. Issues in the use of inhaled glucocorticoids. Am J Respir Crit Care Med 1996;153:1739–48) recommend on going treatment for 80% of these asthma patients with inhaled corticosteroids or glucocorticoids (IGC). The device of choice for administration of these inhaled corticosteroids is a metered dose inhaler.

It is well established that IGC are effective in the treatment of asthma. (Kamada et al. Issues in the use of inhaled glucocorticoids. Am J Respir Crit Care Med 1996;153: 1739–48). However, IGC have the potential to cause severe adverse systemic effects. For example chronic long term use of IGC has been reported to cause adrenal suppression, osteoporosis and growth suppression in children (Doull et al. Growth of asthmatic children on inhaled corticosteroids (abstract). Am Rev Respir Dis 1993;147:A265, Littlewood J M, Johnson A W, Edwards P A, et al. Growth retardation in asthmatic children treated with inhaled beclomethasone dipropionate. Lancet 1988;i:115–6, Wales J K H, Barnes N D, Swift P G F. Growth retardation in children on steroids in asthma. Lancet 1991;338:1535–6, Wolthers O D, Pederson S. Controlled study of linear growth in asthmatic children during treatment with inhaled corticosteroids. Pediatrics 1992;89:839–42, Wolthers O D, Pederson S. Short-term growth during treatment with inhaled fluticasone propionate and beclomethasone dipropionate. Arch Dis Child 1993;68: 673–6, Prifitsk K, Milner A D, Conway E, et al. Adrenal function in asthma. Arch Dis Child 1990;65:838–40). The danger of these adverse effects increases with the amount of IGC consumed (Dahl R, Lundback B, Malo J-L. A dose ranging study of fluticasone propionate in adult patients with moderate asthma. Chest 1993;104:1352–8).

Studies indicate that dose-dependent suppression of the hypothalamic-pituitary-adrenal axis (HPAA) occurs in both healthy volunteers and in asthmatics (Nikolaizik et al. Nocturnal cortisol secretion in healthy adults before and after inhalation of budesonide. Am J Respir Crit Care Med 1996;153:97–101, Donnelly et al. Effects of budesonide and fluticasone on 24-hour plasma cortisol. Am J Respir Crit Care Med 1997;156:1746–51). This suppression occurs even following a single dose inhalation of IGC. Systemic bioavailability of IGC is a function of absorption of the drug across the lung vascular bed. Lung deposition and systemic bioavailability are altered airway diameter in patients with asthma. Further, the degree of narrowing varies widely, both among patients within the population and as a function of time for each individual patient (Weiner et al. Characteristics of asthma in the elderly. Eur Respir J 1998;12 (3):564–8).

Thus, the inability of standard IGC therapy regimens employing fixed dose metered dose inhalers to customize the dose to the requirements of an individual patient at a specific time poses a significant risk to many asthma patients.

Although current guidelines on asthma treatment recommend the administration of the lowest dose of IGC compatible with asthma control, computation of this dose is most often based upon analysis of responses of a large population of patients. In cases where individual patients have their pulmonary function quantitatively analyzed, such analyses are generally performed periodically, not daily or prior to each inhalation of IGC.

Further, it is widely believed by clinicians that improved asthma control can be achieved by increasing the dose of IGCs. Thus, there is a tendency to empirically determine how much IGC is required to provide relief from an acute asthma attack and advise patients to continue to apply this high dosage. Such practice ignores the idea that the dose of IGC should be reduced as soon as control is achieved. This is because the tendency for each unit of IGC delivered to the airway to exert a systemic effect increases as the patients condition stabilizes or improves.

U.S. Pat. No. 5,724,986 issued to Jones Jr. et al teaches a casing and spirometer for a metered dose inhaler. Jones Jr. teaches measurement of a pulmonary parameter such as peak expiratory flow (PEF). However, Jones Jr. fails to teach use of this measurement to compute a minimum effective dose. Instead, Jones Jr. teaches determination of an optimum time to release medication from a metered dose inhaler. According to the teachings of Jones Jr., the optimum time is chosen to insure maximum delivery of the inhaled medication to the lungs (as opposed to the upper airway) regardless of the physiologic condition of the patient. Thus the teachings of Jones Jr. increase the amount of medication delivered systemically and increase the risks associated with systemic administration of medication.

U.S. Pat. No. 5,826,570 issued to Goodman et al. teaches delivery of aerosol medications for inspiration. Goodman, like Jones Jr., teaches determination of an optimum time to release medication from a metered dose inhaler. Goodman teaches choosing a desired location for deposition of the inhaled medication. Like Jones Jr., Goodman teaches maximization of the respirable fraction of the aerosolized medication. Thus, like Jones Jr., Goodman teaches increasing the amount of medication delivered systemically thereby increasing the risks associated with systemic administration of medication. Further, Goodman teaches calculations based upon repeated measurements. This is an inherent disadvantage because it increases the amount of time required for a patient to measure pulmonary function prior to beginning treatment.

There is thus a need for, and it would be highly advantageous to have, systems and methods for determining a minimum effective dose of an inhaled drug for an individual patient at a given time devoid of the above limitations.

SUMMARY OF THE INVENTION

According to one aspect of the present invention there is provided a system for determining a minimum effective dose of an inhaled drug for an individual patient at a given time. The system includes: (a) a measuring apparatus designed and constructed to measure at least one pulmonary performance indicator measurement of the individual patient and (b) a data processor capable of communication with the measuring apparatus, the data processor designed and configured to provide a computed minimum effective dose for the individual patient by applying a predetermined rule to the pulmonary performance indicator measurement.

According to another aspect of the present invention there is provided a method of optimizing a dose of an inhaled drug to an individual patient at a given time. The method includes: (a) measuring at least one pulmonary performance indicator measurement of the individual patient; (b) communicating the pulmonary performance indicator measurement to a data processor; and (c) computing a minimum effective dose for the individual patient by applying a predetermined rule to the pulmonary performance indicator measurement within the data processor.

According to yet another aspect of the present invention there is provided an article of manufacture for autonomous individual optimization of a treatment protocol for an individual patient suffering from a respiratory disorder. The article of manufacture includes (a) a measuring apparatus designed and constructed to measure at least one pulmonary performance indicator measurement of the individual patient, (b) a data processor capable of communication with the measuring apparatus, the data processor designed and configured to provide a computed minimum effective dose for the individual patient by applying a predetermined rule to the pulmonary performance indicator measurement, (c) an adjustable delivery mechanism designed and constructed to receive the computed minimum effective dose and to to deliver the computed minimum effective dose of the inhaled drug to the individual patient, (d) a pharmaceutical composition identified for treatment of the respiratory disorder being contained within the adjustable delivery mechanism, the pharmaceutical composition including, as an active ingredient, an agent capable of relieving symptoms of the respiratory disorder and packaging material.

According to further features in preferred embodiments of the invention described below, the system includes an adjustable delivery mechanism capable of communicating with the data processor and receiving the computed minimum effective dose, the delivery mechanism designed and constructed to deliver the computed minimum effective dose of the inhaled drug to the individual patient.

According to still further features in the described preferred embodiments the system includes an adjustable delivery mechanism designed and constructed to receive the computed minimum effective dose as a manual data input, the delivery mechanism designed and constructed to deliver the computed minimum effective dose of the inhaled drug to the individual patient.

According to still further features in the described preferred embodiments the measuring apparatus is selected from a group consisting of a spirometer and a mechanical peak flow meter.

According to still further features in the described preferred embodiments the pulmonary performance indicator is selected from a group consisting of forced expiratory volume in one second (FEV1) and peak expiratory flow (PEF).

According to still further features in the described preferred embodiments the computed minimum effective dose is presented in a format selected from a group consisting of actual quantitative units and arbitrary units.

According to still further features in the described preferred embodiments the predetermined rule includes:

$$y = -17.183 + 0.645 \left\{ \frac{\text{measured } FEV1}{\text{anticipated } FEV1} \times 100 \right\}$$

wherein y is the percentage of drugs absorbed/cortisol production.

According to still further features in the described preferred embodiments the predetermined rule for determining a computed minimum effective dose Z (in micrograms) includes:

$$Z = BD - \{BD \times ([MFRP - BFRP]/100)\} \times 0.645$$

wherein BD indicates a basic dose at the beginning of treatment, MFRP indicates a measured FEV1 relative percentage and wherein BFRP indicates a basic FEV1 Relative Percentage (100% is the normal) when the BD is determined. MFRP may be determined anytime while consuming medication.

According to still further features in the described preferred embodiments the adjustable delivery mechanism includes at least one item selected from a group consisting of a mechanical dispenser, an electromechanical dispenser (e.g. QX4C-N manufactured by T.M.M. Motion and Magnetic Technologies, Tel-Aviv, Israel) and a piezo-electric dispenser (e.g. STM manufactured by Nanomotion Ltd, Yokneam, ISRAEL). According to various embodiments of the invention, the delivery mechanism may deliver either a powder or aerosolized liquid droplets.

According to still further features in the described preferred embodiments the method further includes: (d) transmitting the minimum effective dose to an adjustable delivery mechanism from the data processor via a channel of communication between the adjustable delivery mechanism and the data processor; and (e) permitting the adjustable delivery mechanism to automatically adjust to deliver the minimum effective dose of the inhaled drug to the individual patient and to deliver the minimum effective dose.

According to still further features in the described preferred embodiments the method further includes: (d) manually inputting the minimum effective dose to an adjustable delivery mechanism; and (e) delivering the minimum effective dose of the inhaled drug to the individual patient by means of the adjustable delivery mechanism.

According to still further features in the described preferred embodiments the measuring is accomplished by a device selected from a group consisting of a spirometer and a mechanical peak flow meter.

According to still further features in the described preferred embodiments the adjustable delivery mechanism receives the computed minimum effective dose from the data processor automatically.

According to still further features in the described preferred embodiments the measuring apparatus, the data processor and the adjustable delivery mechanism are integrally formed together or connected one to another.

According to still further features in the described preferred embodiments the measuring apparatus and the data processor are integrally formed together or connected one to another and the adjustable delivery mechanism is connectable thereto.

The present invention successfully addresses the shortcomings of the presently known configurations by providing systems and methods for determining a minimum effective dose of an inhaled drug for an individual patient at a given time based upon results of a single measurement of a pulmonary performance indicator immediately prior to inhalation of the medication.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of systems and methods for determining a minimum effective dose of an inhaled drug for an individual patient at a given time which can reduce the risks associated with chronic long term use of inhaled drugs. Systems according to the present invention may optionally be supplied as articles of manufacture.

Specifically, the present invention can be used to compute, and optionally deliver, a minimum effective dose of an inhaled medication based upon results of a single measurement of a pulmonary performance indicator immediately prior to inhalation of the medication. The invention is expected to find especial utility in care and treatment of chronic asthma patients by reducing the total amount of glucocorticoids inhaled over a period of time. This reduction in glucocorticoid consumption is capable of reducing the adverse impact of coticosteroid compounds.

The principles and operation of systems and methods for determining a minimum effective dose of an inhaled drug according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1:
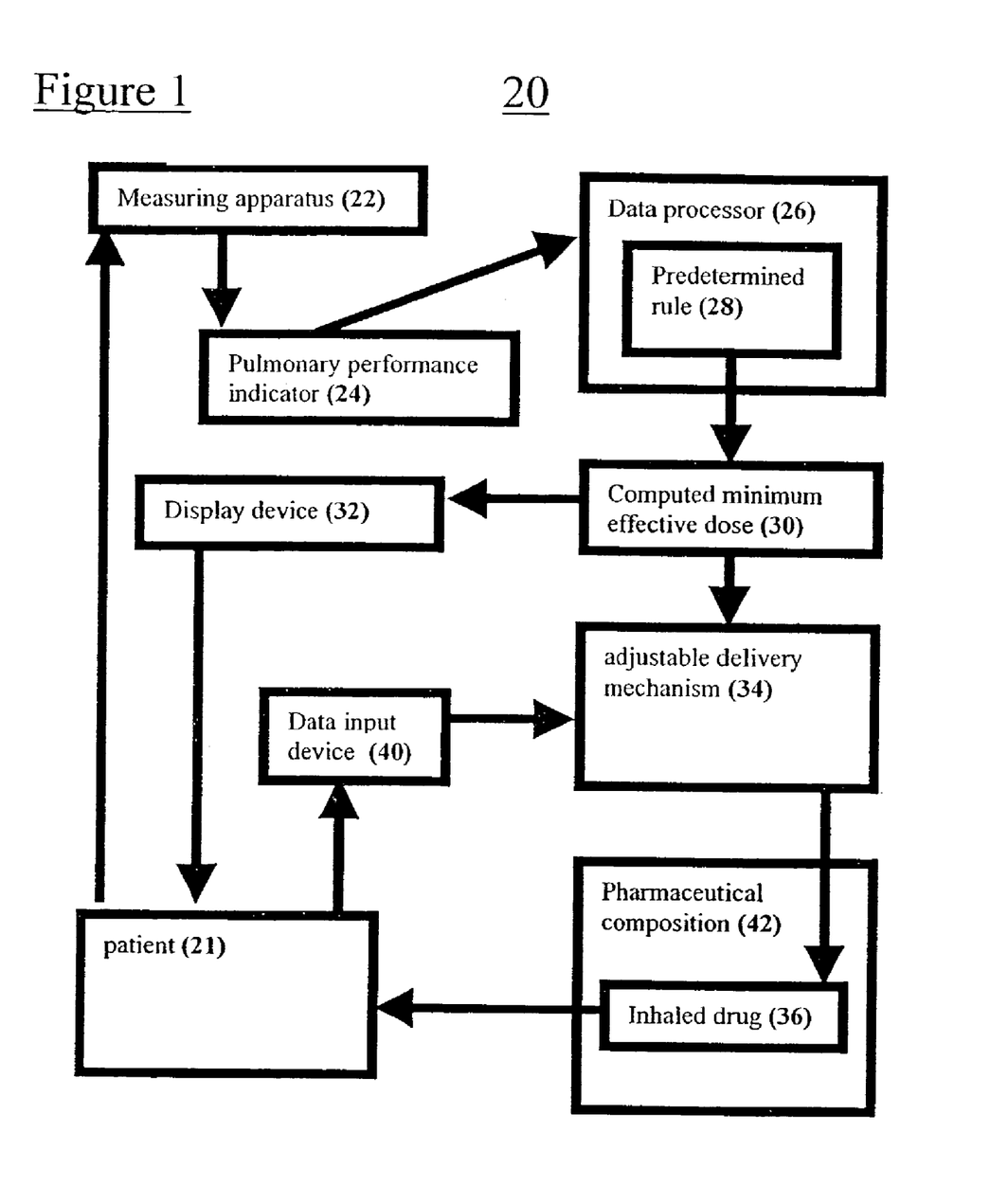
FIG. 1 is a schematic representation of a system for determining a minimum effective dose of an inhaled drug for an individual patient at a given time according to the present invention.
Figure 3A:
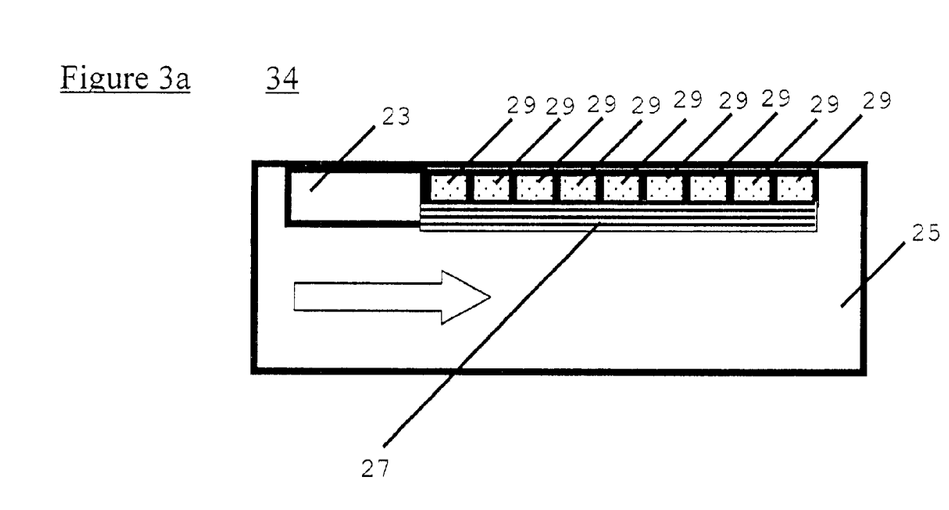
FIGS. 3a and 3b are side cut away views illustrating operation of one embodiment of an adjustable delivery mechanism suited for use in the context of the present invention.
Figure 3B:
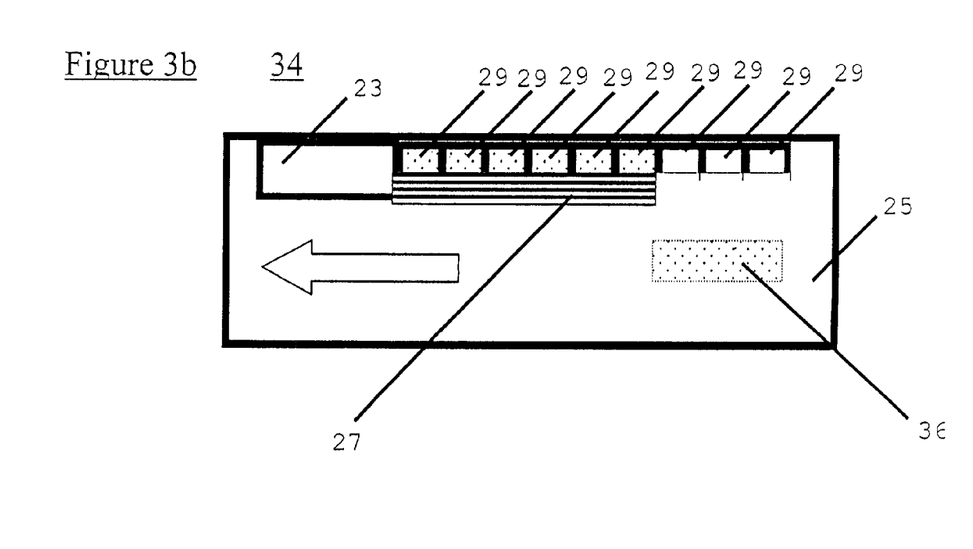

Referring now to the drawings, FIG. 1 illustrates a system 20 for determining a minimum effective dose of an inhaled drug 36 for an individual patient 21 at a given time. System 20 includes a measuring apparatus 22 designed and constructed to measure at least one pulmonary performance indicator measurement 24 of an individual patient 21. Measuring apparatus 22 may be, for example, a spirometer or a mechanical peak flow meter. Patient 21 would thus exhale into air passage 25 (see FIGS. 3a, 3b and 5) in order to measure pulmonary performance indicator 24. Pulmonary performance indicator measurement 24 may be, for example, forced expiratory volume in one second (FEV1) or peak expiratory flow (PEF). System 20 further includes a data processor 26 capable of communication with measuring apparatus 22 for purposes of receiving pulmonary performance indicator measurement 24 there from. Communication may be effected through any channel of communication including, but not limited to, a wired connection, an infrared frequency transmission connection, a local area network connection, a radio frequency connection, a fiber-optic connection or an electromagnetic connection.

Thus, according to some preferred embodiments of the invention, measuring apparatus 22 and data processor 26 are integrally formed together and connected, for example, by a wired connection. More preferably, data processor 26 is incorporated into measuring apparatus 22 as, for example, a microchip or printed circuit.

In some instances it may de desirable to incorporate an existing data processor, such as a personal computer or personal digital assistant, into system 20 as data processor 26. Alternately, but also preferably, measuring apparatus 22 and data processor 26 are separate units which are connectable, for example by a wire, a local area network connection, or a fiber-optic connection for purposes of communication.

Alternately, but also preferably, measuring apparatus 22 and data processor 26 are separate units which communicate without benefit of a physical connection by means of, for example, an infrared frequency transmission connection, a radio frequency connection, or an electromagnetic connection.

Regardless of the physical relationship between measuring apparatus 22 and data processor 26, data processor 26 is designed and configured to provide a computed minimum effective dose 30 for individual patient 21 by applying a predetermined rule 28 to pulmonary performance indicator measurement 24.

Depending upon the exact configuration of system 20, it may be advantageous to present computed minimum effective dose 30 as actual quantitative units (e.g. μg or IU) or arbitrary units (e.g. numerals or letters). In reducing the present invention to practice it has been discovered that a linear relationship (FIG. 5) exists between {cortisol drugs absorbed/cortisol produced×100} and observed FEV1 expressed as a percentage of normal (i.e. expected) FEV1. The correlation between these expressions is linear ($R2=0.865$; $P\leq 0$.). Thus it is useful to employ a predetermined rule which includes Equation 1 or Equation 2 or a combination thereof for purposes of configuring data processor 26 of system 20.

Figure 5:
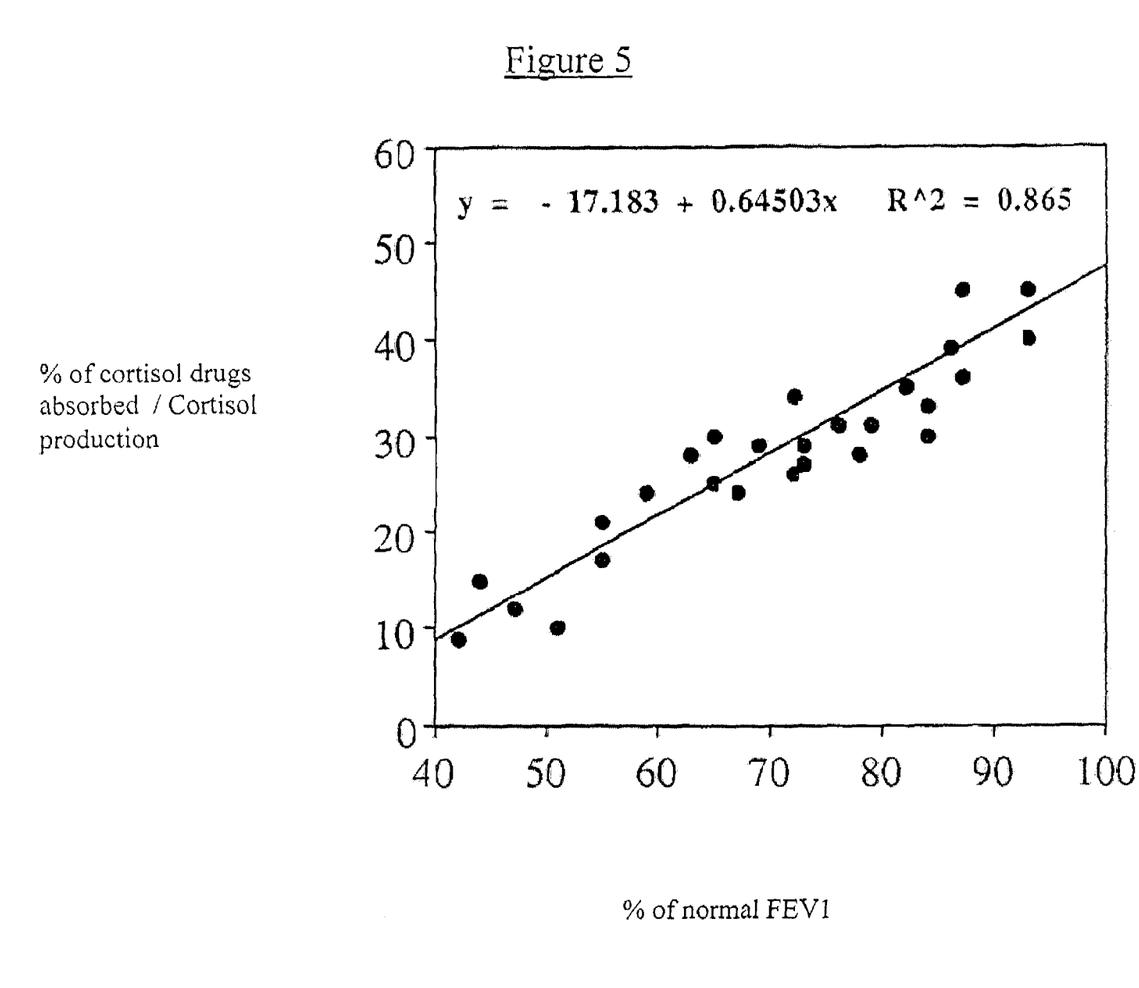
FIG. 5 is graph % cortisol drugs absorbed/cortisol production as a function of % of normal FEV1.

Relation of FEV1 to drugs absorbed/cortisol production is summarized in EQUATION 1:

$$y = -17.183 + 0.645 \left\{ \frac{\text{measured } FEV1}{\text{anticipated } FEV1} \times 100 \right\}$$

wherein y is the percentage of drugs absorbed/cortisol production.

Determination of a computed minimum effective dose Z (in micrograms) is accomplished by EQUATION 2:

$$Z = BD - \{BD \times ([MFRP-BFRP]/100)\} \times 0.645$$

wherein BD indicates a basic dose at the beginning of treatment, MFRP indicates a measured FEV1 relative percentage and wherein BFRP indicates a basic FEV1 Relative Percentage (100% is the normal) when the BD is determined. MFRP may be determined anytime while consuming medication.

System 20 may further include an adjustable delivery mechanism 34 capable of communicating with data processor 26 and receiving computed minimum effective dose 30. Delivery mechanism 34 is designed and constructed to deliver computed dose 30 of inhaled drug 36 to individual patient 21. Inhaled drug 36 is often supplied in the form of a pharmaceutical composition 42 including additional ingredients. It is expected that during the life of this patent many relevant adjustable delivery mechanisms will be developed and the scope of the term "adjustable delivery mechanism" is intended to include all such new technologies a priori.

Alternately, but also preferably adjustable delivery mechanism 34 is designed and constructed to receive computed minimum effective dose 30 as a manual data input by means of a data input device 40 (FIG. 4) on delivery mechanism 34. In this case, computed dose 30 is displayed on display device 32 and observed by patient 21. For purposes of the specifications and the accompanying claims the phrase "display device" refers to any device for presentation of data to a patient. The definition includes, but is not limited to mechanical displays, speakers, LCD screens, LED displays, CRT displays and active matrix displays.

Figure 4:
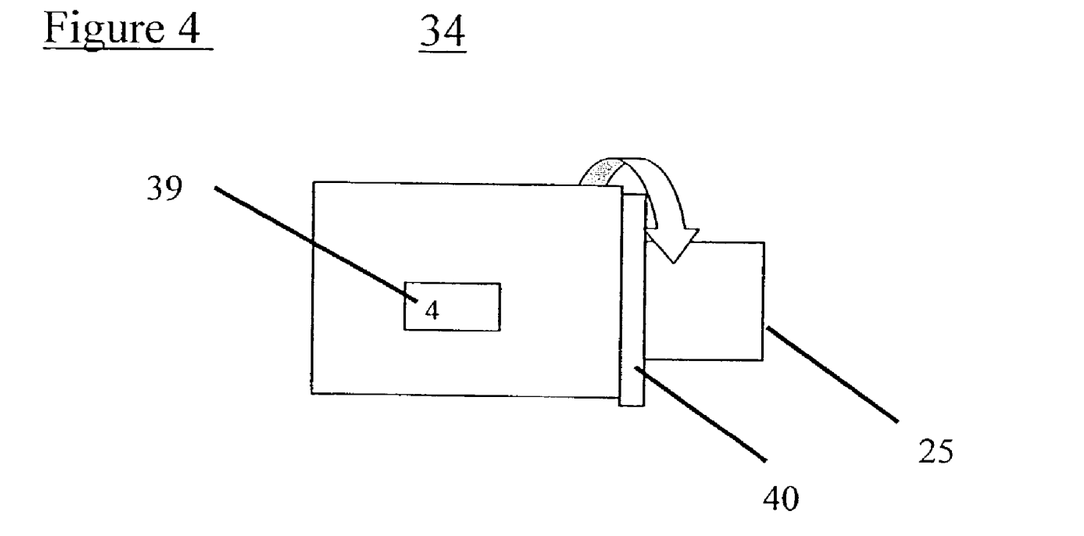
FIG. 4 is a side view of an adjustable delivery mechanism suited for use in the context of the present invention.

Patient 21 the inputs computed dose 30 into input device 40 on delivery mechanism 34. Delivery mechanism 34 is further designed and constructed to deliver computed minimum effective dose 30 of inhaled drug 36 to individual patient 21 either as a result of the manual data input via input device 40 or as a result of subsequent actuation of delivery mechanism 34. FIG. 4 shows display 39 of data input in arbitrary units. In the pictured embodiment of delivery mechanism 34, input device 40 is a rotating ring (rotation depicted by curved arrow). Each increment of rotation is depicted on display 39 (e.g. as the number 4 on an arbitrary scale from 1–7. Examination of display 39 helps patient 21 to ascertain that they have correctly input computed dose 30 to delivery mechanism 34. While numerals are pictured in FIG. 4, it may be advantageous to express computed dose 30 in non-numerical units (e.g. colors, letters, animals, geometric forms) in order to prevent patient 21 from being aware of the size of dose 30.

Adjustable delivery mechanism 34 may include, for example, a mechanical dispenser, an electronic dispenser, an electromechanical dispenser, a piezo-electric dispenser or an aerosol dispenser or combinations including at least one of these dispenser types. Delivery mechanism 34 may deliver aerosolized droplets or powder.

The present invention is additionally embodieed by a method 50 (FIG. 2) of optimizing a dose 30 of an inhaled drug 36 to an individual patient 21 at a given time. Method 50 includes measuring 52 at least one pulmonary performance indicator measurement 24 of individual patient 21. Measuring 52 is preferably accomplished a spirometer or a mechanical peak flow meter, although other devices could be employed without significantly effecting method 50 or an outcome thereof. Method 50 further includes communicating 54 pulmonary performance indicator measurement 24 to data processor 26 and computing 56 minimum effective dose 30 for individual patient 21 by applying predetermined rule 28 to pulmonary performance indicator measurement 24 within e data processor 26.

Figure 2:
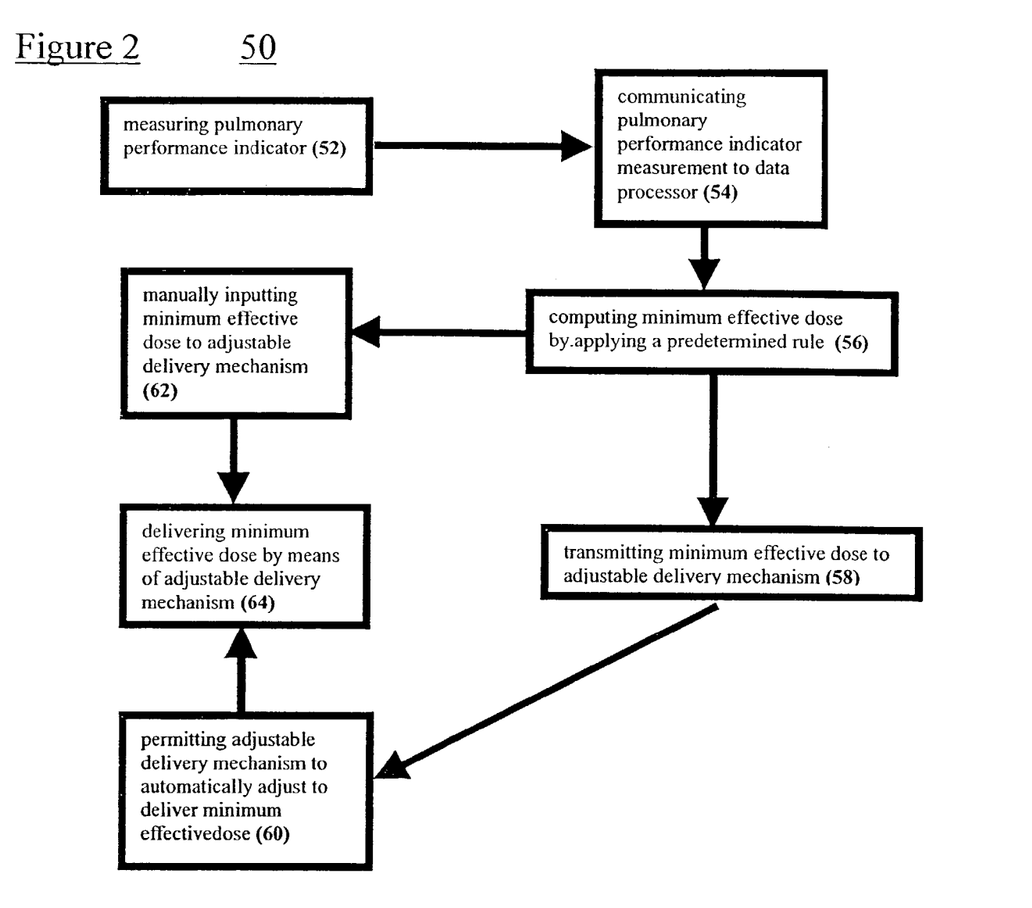
FIG. 2 is a simplified flow diagram illustrating possible sequences of events in performance of a method of determining a minimum effective dose of an inhaled drug for an individual patient at a given time according to the present invention.

Optionally, but preferably, method 50 further includes transmitting 58 minimum effective dose 30 to adjustable delivery mechanism 34 from data processor 26 via a channel of communication between adjustable delivery mechanism 34 and data processor 26 and permitting 60 adjustable delivery mechanism 34 to automatically adjust to deliver the minimum effective dose of inhaled drug 36 to individual patient 21 and to deliver 64 the minimum effective dose 30 to patient 21.

Alternately, but also preferably, method 50 further includes manually inputting 62 minimum effective dose 30 to adjustable delivery mechanism 34 and delivering 64 minimum effective dose 30 of inhaled drug 36 to individual patient 21 by means of adjustable delivery mechanism 34.

System 20 is optionally, but preferably supplied as an article of manufacture for autonomous individual optimization of a treatment protocol for an individual patient suffering from a respiratory disorder (e.g. asthma) "Optimization" as used herein refers to optimization at a specific point in time. That is, patient 21 computes 56 an optimum dose 30 immediately prior to each use of inhaled drug 36. The article of manufacture includes measuring apparatus 22, data processor 26 and adjustable delivery mechanism 34 as described hereinabove. According to this embodiment of the invention, adjustable delivery mechanism 34 contains pharmaceutical composition 42 identified for treatment of the respiratory disorder and including, as an active ingredient, an agent 36 capable of relieving symptoms of the respiratory disorder and packaging material.

Pharmaceutical composition 42 may contain a "physiologically acceptable carrier" which, as used herein, refers to a carrier or a diluent that does not cause significant irritation to an organism and does not abrogate the biological activity and properties of administered compound 36. An adjuvant is included within this definition.

Pharmaceutical composition 42 may further contain an "excipient" which, as used herein, refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

For administration by nasal or oral inhalation, the active ingredients for use according to the present invention may be conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount.

Articles of manufacture of the present invention may, if desired, be presented in a pack, such as an FDA approved kit, which may contain one or more unit dosage forms containing active ingredient 36. The pack may, for example, comprise metal or plastic foil, such as a blister pack. The pack may be accompanied by instructions for measurement and administration. The pack may also include a notice associated with the container in a form prescribed by a governmental agency regulating the manufacture, use or sale of pharmaceuticals, which notice is reflective of approval by the agency of the form of the compositions or human administration. Such notice, for example, may be of labeling approved by the U.S. Food and Drug Administration for prescription drugs or of an approved product insert.

Preferably the article of manufacture is designed and constructed so that adjustable delivery mechanism 34 receives computed minimum effective dose 30 from data processor 26 automatically.

According to some preferred embodiments of the invention, measuring apparatus 22, data processor 22 and adjustable delivery mechanism 34 are integrally formed together or connected one to another.

According to alternate preferred embodiments of the invention measuring apparatus 22 and data processor 26 are integrally formed together or connected one to another and adjustable delivery mechanism 34 is connectable thereto.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

As an illustrative, non-limiting, example of the potential benefit of a systems 20 and methods 50 according to the present invention, consider the case of a hypothetical asthma patient Ms. Bea Wreatheshard. Bea has been treated in the past with a standard metered doses inhaler which delivers 50 micrograms of an IGC based drug per actuation. Her doctor has instructed her to inhale two actuations in the morning upon arising and two actuations before retiring at night. As a result, Bea inhales 200 micrograms/day of IGC or 6 milligrams every thirty days.

According to the present invention, measuring apparatus 22 would measure a pulmonary performance indicator 24 before each treatment. Data processor 26 would apply a predetermined rule 28 to determine a minimum effective dose 30 (e.g. Z according to equation 2) specifically for Bea at the specific time she is going to be treated. Dose 30 may sometimes be greater than 100 micrograms but will generally be less than 100 micrograms. As a result, Bea will consume well below 6 milligrams per month of IGC although she will feel better because dose 30 will be in excess of 100 micrograms when Bea is suffering most from Asthma. On days when Bea is breathing normally, she will still actuate delivery mechanism 34 4 times but may receive no medication at all. Further, according to preferred embodiments of the invention, Bea will be unaware of the dose 30 she is receiving. This may be accomplished, for example, by use of an automated delivery mechanism 34 with no display or by use of display device 32 and data input device 34 which employ non-alphanumeric symbols. For example, names of classical music composers or animals might be employed to indicate different dosage levels. As a result, stress, which is believed to be a contributing factor in Asthma, is reduced. Thus, as a result of the present invention, Bea benefits from reduced IGC consumption, an increased feeling of wellness and reduced stress.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for determining a minimum effective dose of an inhaled drug for an individual patient at a given time, the system comprising:
   (a) a measuring apparatus designed and constructed to measure at least one pulmonary performance indicator measurement of the individual patient; and
   (b) a data processor capable of communication with said measuring apparatus, said data processor designed and configured to provide a computed minimum effective dose for the individual patient by applying a predetermined rule to said pulmonary performance indicator measurement; and
   (c) an adjustable delivery mechanism capable of communicating with said data processor and receiving said computed minimum effective dose, said delivery mechanism designed and constructed to deliver said computed minimum effective dose of the inhaled drug to the individual patient.

2. The system of claim 1, wherein said measuring apparatus is selected from a group consisting of a spirometer and a peak flow meter.

3. The system of claim 1, wherein said pulmonary performance indicator is selected from a group consisting of forced expiratory volume in one second (FEV1) and peak expiratory flow (PEF).

4. The system of claim 1, wherein said computed minimum effective dose is presented in a format selected from a group consisting of actual quantitative units and arbitrary units.

5. The system of claim 1, wherein said pulmonary performance indicator measurement is forced expiratory volume in one second (FEV1) wherein said predetermined rule includes a linear relationship between the forced expiratory volume in one second (FEV1) and the computed minimum effective dose.

6. The system of claim 1, wherein said adjustable delivery mechanism includes at least one item selected from a group consisting of a mechanical dispenser, an electromechanical dispenser and a piezo-electric dispenser.

7. A system for determining a minimum effective dose of an inhaled drug for an individual patient at a given time, the system comprising:
（a) a measuring apparatus designed and constructed to measure at least one pulmonary performance indicator measurement of the individual patient; and
(b) a data processor capable of communication with said measuring apparatus, said data processor designed and configured to provide a computed minimum effective dose for the individual patient by applying a predetermined rule to said pulmonary performance indicator measurement; and
(c) an adjustable delivery mechanism designed and constructed to receive said computed minimum effective dose as a manual data input, said delivery mechanism designed and constructed to deliver said computed minimum effective dose of the inhaled drug to the individual patient.

8. The system of claim 7, wherein said adjustable delivery mechanism includes at least one item selected from a group consisting of a mechanical dispenser, an electromechanical dispenser and a piezo-electric dispenser.

9. The system of claim 7, wherein said measuring apparatus is selected from a group consisting of a spirometer and a peak flow meter.

10. The system of claim 7, wherein said pulmonary performance indicator is selected from a group consisting of forced expiratory volume in one second (FEV1) and peak expiratory flow (PEF).

11. The system of claim 7, wherein said pulmonary performance indicator measurement is forced expiratory volume in one second (FEV1) wherein said predetermined rule includes a linear relationship between the forced expiratory volume in one second (FEV1) and the computed minimum effective dose.

12. The system of claim 7, wherein said adjustable delivery mechanism includes at least one item selected from a group consisting of a mechanical dispenser, an electromechanical dispenser and a piezo-electric dispenser.

* * * * *